(12) United States Patent
Korten et al.

(10) Patent No.: US 10,040,134 B2
(45) Date of Patent: Aug. 7, 2018

(54) METHOD OF PRODUCING A DENTAL RESTORATION

(71) Applicant: 3M INNOVATIVE PROPERTIES COMPANY, St. Paul, MN (US)

(72) Inventors: Malte Korten, Moorenweis (DE); Daniel Oberpertinger, Gauting (DE); Rudolf Schmid, Eichenau (DE); Anja B. Fischer, Hechendorf (DE)

(73) Assignee: 3M INNOVATIVE PROPERTIES COMPANY, S. Paul, MN (US)

( * ) Notice: Subject to any disclaimer, the term of this patent is extended or adjusted under 35 U.S.C. 154(b) by 648 days.

(21) Appl. No.: 14/425,148

(22) PCT Filed: Aug. 22, 2013

(86) PCT No.: PCT/US2013/056162
§ 371 (c)(1),
(2) Date: Mar. 2, 2015

(87) PCT Pub. No.: WO2014/039268
PCT Pub. Date: Mar. 13, 2014

(65) Prior Publication Data
US 2015/0230896 A1    Aug. 20, 2015

(30) Foreign Application Priority Data
Sep. 4, 2012  (EP) .................................. 12183003

(51) Int. Cl.
*A61C 13/00*     (2006.01)
*A61C 13/083*    (2006.01)
(Continued)

(52) U.S. Cl.
CPC ............ *B23C 3/00* (2013.01); *A61C 13/0006* (2013.01); *A61C 13/0022* (2013.01);
(Continued)

(58) Field of Classification Search
CPC . A61C 13/0004; A61C 13/083; A61C 13/082; A61C 13/0022; A61C 13/0006;
(Continued)

(56) References Cited

U.S. PATENT DOCUMENTS 4,588,443 A    5/1986  Bache
4,751,099 A    6/1988  Niino
(Continued)

FOREIGN PATENT DOCUMENTS

AT    000582    1/1996
AU    6963287   9/1987
(Continued)

OTHER PUBLICATIONS

International Search Report for PCT International Application No. PCT/US2013/056162 dated Nov. 13, 2013 4 pages.

*Primary Examiner* — Robert J Grun

(57) ABSTRACT

The present invention relates to a method of producing a dental restoration from a partially-sintered or non-sintered blank using a three-dimensional dental restoration model, comprising the steps of: generating at least one or more first milling path for rough and/or fine milling; determining areas or zones of increased stress in the three-dimensional dental restoration model and generating at least one modified milling path; machining the blank by milling utilizing one or more first milling paths; selectively machining parts of the blank utilizing at least one modified milling path; and sintering the machined blank.

17 Claims, 4 Drawing Sheets

(51) Int. Cl.
*B23C 3/00* (2006.01)
*A61C 13/08* (2006.01)

(52) U.S. Cl.
CPC .......... *A61C 13/082* (2013.01); *A61C 13/083* (2013.01); *B23C 2220/605* (2013.01); *B23C 2226/18* (2013.01)

(58) Field of Classification Search
CPC .. B23C 3/00; B23C 2220/605; B23C 2226/18
See application file for complete search history.

(56) References Cited

U.S. PATENT DOCUMENTS

| | | | |
|---|---|---|---|
| 5,106,303 | A | 4/1992 | Oden |
| 5,217,375 | A | 6/1993 | Oden |
| 5,352,643 | A | 10/1994 | Staehler |
| 5,389,590 | A | 2/1995 | Nawa |
| 5,520,323 | A | 5/1996 | Hauner |
| 5,651,901 | A | 7/1997 | Mohri |
| 5,656,391 | A | 8/1997 | Hambitzer |
| 5,705,794 | A | 1/1998 | Gillespie |
| 5,765,667 | A | 6/1998 | Roess |
| 5,873,402 | A | 2/1999 | Nechansky |
| 6,057,004 | A | 5/2000 | Oppawsky |
| 6,454,629 | B1 | 9/2002 | Basler |
| 8,048,345 | B2 | 11/2011 | Feith |
| 2005/0177266 | A1 | 8/2005 | Kopelman |
| 2008/0241794 | A1 | 10/2008 | Urata |
| 2010/0058588 | A1 | 3/2010 | Heinz |
| 2012/0143364 | A1* | 6/2012 | Mcleod .................. A61C 1/082 700/98 |
| 2012/0148985 | A1 | 6/2012 | Jung |

FOREIGN PATENT DOCUMENTS

| | | |
|---|---|---|
| CA | 2038833 | 9/1991 |
| DE | 4112936 | 10/1991 |
| DE | 4401589 | 8/1994 |
| DE | 19651557 | 6/1998 |
| DE | 102005001600 | 6/2006 |
| EP | 0477157 | 3/1992 |
| EP | 1066801 | 1/2001 |
| JP | 11-277453 | 10/1999 |
| RU | 2054400 | 2/1996 |
| WO | WO 1992-02807 | 2/1992 |
| WO | WO 2000-10509 | 3/2000 |
| WO | WO 2006-105944 | 10/2006 |

* cited by examiner

METHOD OF PRODUCING A DENTAL RESTORATION

TECHNICAL FIELD OF THE INVENTION

The present invention relates to a method of producing a dental restoration. In particular, the present invention relates to a method of producing a ceramic dental restoration using CAD/CAM automation employing a modified milling strategy. The resultant ceramic dental restoration produced according to the modified milling strategy exhibits increased fracture strength and toughness, and has fewer surface defects.

BACKGROUND

Dental restorations, such as crowns, bridges, implants, dentures and tooth replacements, can be produced by a number of different manufacturing processes using various materials. In recent years, developments in materials and manufacturing processes have focussed on the production of dental restorations based on ceramic materials. Generally, ceramic dental restorations comprise a base section or support framework which provides the necessary strength, and additionally a facing section or veneer is applied which provides the necessary aesthetic appearance. More recently, the use of monolithic materials in dedicated monolithic zirconia dental restorations has become more commonplace. The advantage of monolithic restorations, that is to say restorations formed of one material instead of a combined framework and veneer structure, is that the dentist or clinician is able to remove less material from the natural tooth because the monolithic zirconia restoration can have a thinner wall thickness compared to other restorations.

The most important properties of ceramic restorations, especially dental zirconia restorations, are the ceramic material's fracture strength and fracture toughness. This is the ability of the material to resist propagation of an internal crack or fracture, and is one of the most important indications of the material's clinical reliability. However, a design compromise is sometimes needed, depending upon the particular clinical situation. In particular, a design needing higher fracture strength limits the aesthetics and the functional parameters of the dental parts. For example, a large connector cross section in an anterior bridge influences the final design and veneering, and limits the natural look of the restoration.

Ceramic restorations are often manufactured using automated CAD/CAM (computer-aided design/computer-aided manufacturing) technology, which typically include a 3D scanning device, a milling machine and a sinter furnace, all of which are controlled by appropriate computer software. The workflow starts with the dentist or clinician taking an impression from the patient and sending this impression to a dental technician. The dental technician builds a plaster model based on the impression and scans this model with the 3D scanner. Based on the scanned data, the dental technician designs a new dental restoration 3D model. This 3D model is the basis for the CAD/CAM process. The dental restoration 3D model is also scaled accordingly to take into account the predicted shrinkage that occurs during the sintering phase.

Typically, the CAM module of prior art systems has, depending on the dental indication, standardised milling strategies. That is to say, for example, every bridge will be machined by calculated milling steps from rough milling to dress/fine milling until the dental part is completed. These steps and milling strategies are calculated individually in the CAM module for each of the dental parts. After the calculation of these steps, the CAM module translates this milling sequence to machine code and this is sent to the particular milling machine for the milling process to commence. After the zirconia restoration is milled, a subsequent sintering stage is then needed to achieve the final shape and mechanical properties.

3M EPSE Lava™ is such a prior art CAD/CAM technology for dental restorations on a zirconium oxide base.

A further prior art technique for milling ceramic dental restorations can be found in WO 2006/105944 A1 which discloses a grinding and polishing tool, and a method for machining ceramic materials, including zirconium oxide.

However, there is still need for improvements, especially with respect to the enhanced requirements of modern dental materials and clinical indications. Significantly increasing the fracture strength of milled zirconia parts, by producing a smoother surface with a reduced number of flaws or surface defects, will considerably expand the clinical indication spectrum of digital restorative dentistry for both monolithic restorations and combined framework and veneer structures. For example, it is desirable to be able to produce a highly aesthetic low cross section anterior bridge restoration, which has been difficult to achieve using known CAD/CAM technology.

Moreover, there is a need for a process which allows the manufacturing of ceramic dental restorations in a simple, timely and efficient manner.

SUMMARY OF THE INVENTION

The present invention aims to address these issues by providing a method of producing a dental restoration from a partially-sintered or non-sintered blank using a three-dimensional dental restoration model, comprising the steps of:
  generating at least one or more first milling path for rough and/or fine milling;
  determining areas or zones of increased stress in the three-dimensional dental restoration model and generating at least one modified milling path;
  machining the blank by milling utilising one or more first milling paths;
  selectively machining parts of the blank utilising at least one modified milling path; and
  sintering the machined blank.

An advantage of using the method is that it is possible to determine the areas or zones of increased stress in the three-dimensional dental restoration model (e.g. the connectors of a bridge restoration) and generate a modified milling strategy to make those areas more stress resistant, with a higher fracture strength and fewer surface defects. Furthermore, this increase in fracture strength is also coupled with a reduction in variance and, therefore, increased manufacturing confidence, reproducibility and quality. A further advantage of using the method is that it gives the dentist or clinician a much greater design freedom. Since it is possible to determine the areas or zones of increased stress in the three-dimensional dental restoration model and generate a modified milling strategy to make those areas effectively more stress resistant, the dentist is able to design smaller connector diameters and smaller wall thickness. Using the method allows the dentist or clinician to design and process dental restorations which simply were not capable of manufacture in the past. Furthermore, the dentist is also able to remove less of the natural tooth structure to prepare the tooth stump for the dental restoration.

Preferably the one or more first milling paths are determined by milling parameters selected from the group consisting of: blank starting materials and properties thereof, desired dental restoration surface quality and geometry, geometry and abrasion of the milling tool, economical parameters, computation time, parameters and specifications of the milling machine.

The step of machining the blank by milling utilising one or more first milling paths may further comprise the steps of:
  determining the one or more first milling paths;
  firstly machining the blank by infeeding a milling tool by a predetermined value in a vertical direction until a lowest milling point of the blank is reached; and
  secondly machining the blank by line-by-line milling.

Preferably the step of selectively machining parts of the blank utilising a modified milling path to produce a milled blank further comprises the step of:
  determining a single second milling path that has a single point of entry between a milling tool and the blank and a single exit point, a cutting edge of the milling tool being in contact with the blank throughout.

Further the step of determining a single second milling path that has a single point of entry between the milling tool and the blank and a single exit point ensures that no area of the blank is machined more than once.

The step of determining a single second milling path that has a single point of entry between the milling tool and the blank and a single exit point may further comprise the step of:
  determining a constant three dimensional step width milling path that is consistent in the direction of a burr removal.

Preferably the single second milling path does not intersect itself.

Further the step of selectively machining parts of the blank utilising a single second milling path ensures that a constant amount of material is removed from the blank.

The step of selectively machining parts of the blank utilising a single second milling path preferably ensures that a cutting force between the tool and the blank is substantially the same and which depends on the geometry of the blank.

Further the step of determining areas or zones of increased stress in the three-dimensional dental restoration model is achieved using finite element analysis.

Preferably the dental restoration is formed from zirconium oxide or aluminum oxide ceramics.

Further the dental restoration is selected from the group consisting of: crowns, bridges, implants, dentures, tooth replacements, inlays, onlays and Maryland bridges.

The three-dimensional dental restoration model may be obtained by scanning a dental impression or by performing an intraoral scan.

The present invention also provides a computer-readable medium having computer-readable instructions which implement the following procedures:
  generating a three-dimensional dental restoration model from scanned dental data;
  generating at least one or more first milling path for rough and/or fine milling a ceramic blank;
  determining areas or zones of increased stress in the three-dimensional dental restoration model and generating at least one modified milling path;
  machining the blank by milling utilising one or more first milling paths;
  selectively machining parts of the blank utilising at least one modified milling path; and sintering the blank.

The present invention also provides a method of producing a dental restoration, comprising the steps of:
  producing a blank;
  machining the blank by milling utilising one or more first milling paths
  selectively machining the blank in areas or zones of increased stress by milling utilising a second milling path that has a single point of entry between a cutting edge of a milling tool and the blank and a single exit point, the cutting edge of the milling tool being in contact with the blank throughout to produce a milled blank; and
  sintering the machined blank.

BRIEF DESCRIPTION OF THE DRAWINGS

The present invention will now be described by way of example only, and with reference to the accompanying drawings, in which.

DETAILED DESCRIPTION OF THE PREFERRED EMBODIMENTS

The present invention has adopted the approach of determining the areas or zones of increased stress in a three-dimensional dental restoration model (e.g. around the connectors of a ceramic bridge restoration) and then generating a modified milling strategy to make those areas more stress resistant with a higher fracture strength with fewer surface defects. Advantageously, this increase in fracture strength is also coupled with a reduction in variance and, therefore, increased manufacturing confidence. Consequently, the use of the present invention will significantly expand the clinical indication spectrum of digital restorative dentistry.

Figure 1:
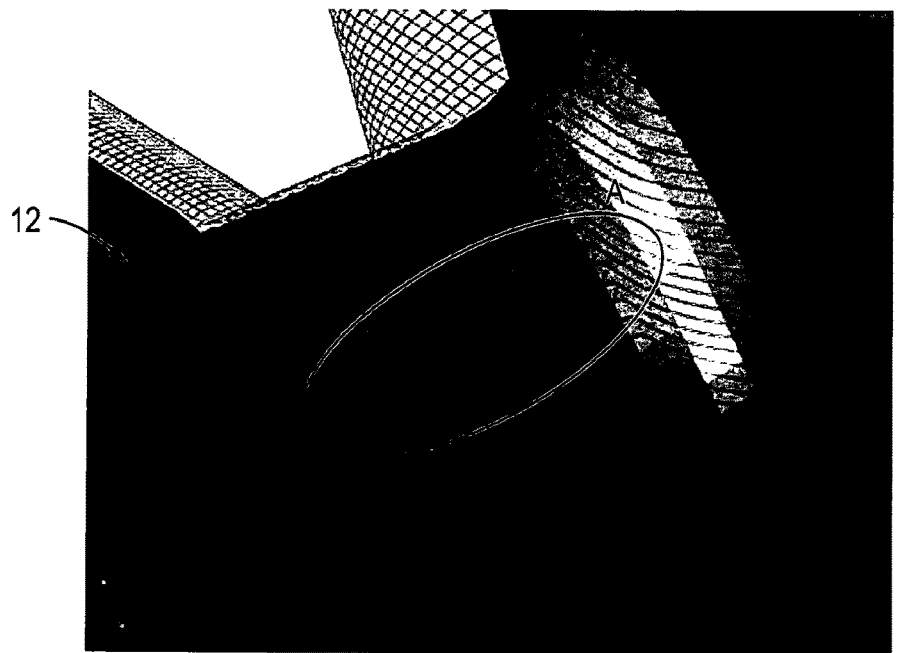
FIG. 1 is a perspective view of a ceramic dental restoration 10 together with its computed prior art milling path 12.

FIG. 1 is a perspective view of a typical ceramic dental restoration 10, along with its computed conventional milling path 12 generated by a CAM module. In order to manufacture an individual ceramic part or restoration 10 in an economical way, the skilled person will appreciate that is necessary to machine the ceramic body in a pre-sintered or at least bindered stage. The milling tracks 12 are calculated by a CAM module and are affected by several parameters including milling tool size and shape, boundaries of milling volume, radial step width, axial step width and the milling strategy which creates the pattern of milling tracks 12. The skilled person will appreciate that the surface of the machined part will have a certain surface roughness and more or fewer flaws or defects depending on the milling tracks 12 and the strategy employed.

Current zirconia milling strategies produce milling paths 12 depending on the restoration 10 geometry and the needed precision. The inner contour of a dental restoration 10 is typically milled more precisely than the outer contour. Furthermore, the milling paths 12 typically change when the surface of the tooth replacement or bridge changes.

In general, a conventional milling process 12 is divided into rough milling and a finishing step. The aim of the rough milling is the efficient removal of material until a predefined material offset remains. The finishing process seeks to enhance the precision and the surface quality of the milled part. The infeeding of steep areas (>30°) is constant in z-direction (vertical direction), meaning that horizontal milling paths are increased by a predefined value in the z-direction after finishing each turn until the lowest point of the geometry is reached.

After that the remaining material in shallow areas <30° would be removed by line-by-line milling to define the final surface. The milling paths 12 generally intersect each other in the range of ±5°. That means the milling tool will go empty (i.e. not remove any material) as the milling proceeds and likely damage the surface of the restoration 10. This conventional milling process described herein is often referred to in the art as a "combined milling strategy" as it includes a combination of rough and fine milling passes.

Figure 2:
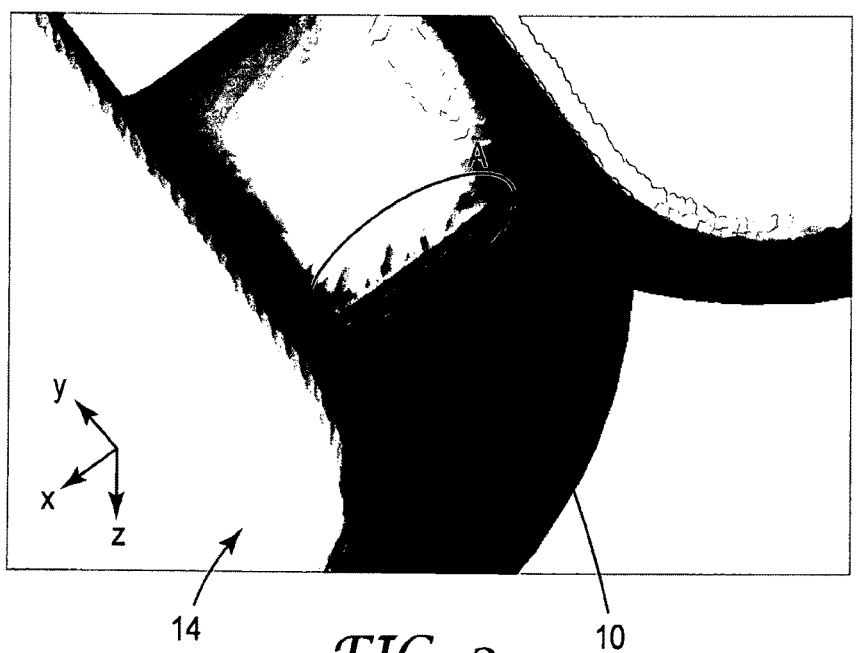
FIG. 2 shows a simulation of a milled ceramic dental restoration 10 having been manufactured using the prior art milling path 12 of FIG. 1.

FIG. 2 shows a simulation of the milled ceramic dental restoration 10 having been manufactured using such a conventional combined milling strategy, as shown in FIG. 1. This simulation was achieved using a proprietary software package, NCSIMUL, manufactured by SPRING Technologies. As can be clearly seen from FIGS. 1 and 2, the use of such a conventional combined milling strategy means that there are milling tracks 12, and simulated milling tracks 14, that intersect each other at numerous places on the restoration 10. These areas are generally highlighted in area A of FIGS. 1 and 2. It has been found that the number and depth of the intersecting milling tracks 12 have a direct influence on the final quality of the machined surface which, in turn, has a direct influence on the fracture strength of the dental restoration 10. A smoother surface with a reduced number of flaws increases the strength of the dental restoration 10.

Figure 3:
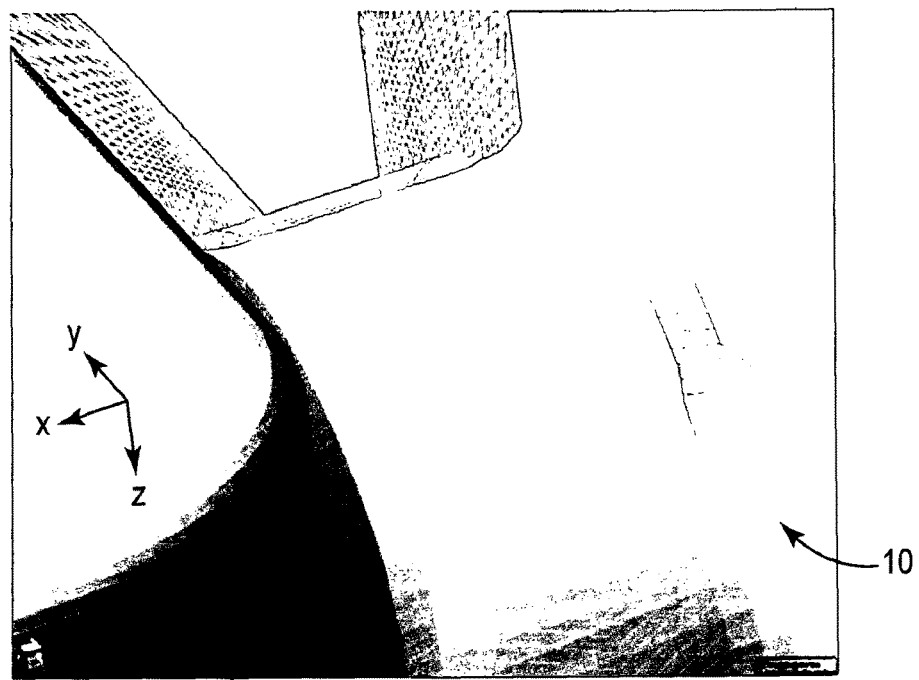
FIG. 3 is a perspective view of a ceramic dental restoration 10 together with its computed modified milling path 16 according to the present invention.

Surprisingly, it has been found that a significant increase in the fracture strength of zirconia ceramic parts can be obtained by adapting the milling process with milling strategies that are known from milling non-ceramic materials. FIG. 3 is a perspective view of such a ceramic dental restoration 10 according to the present invention with its computed modified milling path 16. The ceramic restoration 10 of the present invention can be manufactured using automated CAD/CAM technology, such as the 3M EPSE Lava™ digital dentistry system, which includes a 3D scanning device, a milling tool and a sinter furnace. The workflow starts with the dentist or clinician generating a three-dimensional dental restoration model from a scanned dental impression. The three-dimensional dental restoration model is designed based on scanned data of a plaster model or by using intraoral scans obtained using technology such as the 3M EPSE Lava™ COS. This three-dimensional dental restoration model is the basis for the CAD/CAM process.

As before, the CAM module can develop, depending on the dental indication, standardised milling strategies, including the "combined milling strategy", as described above with reference to FIGS. 1 and 2. That is to say, every bridge or cantilever of the restoration 10 will be machined by calculated milling steps from rough milling to dress/fine milling until the dental part is done. These steps or tracks are calculated individually for each of the dental parts.

The present invention differs from known CAD/CAM processes in that the CAM module is adapted to determine areas or zones of increased or higher stress in the three-dimensional dental restoration model and then to generate a modified milling path for selectively machining the restoration 10 in those areas or zones of increased stress. It has been found that intersecting milling tracks 12 from combined milling strategies are often the cause for early cracks in zirconia parts. By avoiding intersecting milling areas, such as those depicted in FIGS. 1 and 2, the finished restoration 10 according to FIGS. 3 and 4 exhibits a more regular and smoother surface and, as a consequence, an increased fracture strength after sintering.

After the calculation of both the combined 12 and modified milling tracks 16, the CAM module of the present invention translates the complete milling sequence to machine code and this is sent to the milling machine for commencement of the milling process. The milling of the ceramic part 10 then occurs utilising the "combined milling strategy" and the increased or higher stress parts of the three-dimensional dental restoration model are selectively machined utilising the computed "modified milling path".

After the zirconia restoration 10 is milled, a subsequent sintering stage is then needed to achieve the final shape and mechanical properties. The three-dimensional dental restoration model is also scaled accordingly to take into account the predicted shrinkage that occurs during the sintering phase.

Selectively machining parts of the ceramic restoration 10 utilising the modified milling path can be achieved by using what is termed a 3D constant milling strategy. This 3D constant or modified strategy does not divide the surface of the milled part into flat and steep areas. The milling tracks were calculated in a way that none of the areas that have to be machined will be machined twice. Due to this the cutting edge of the tool will always cut some material. Surface defects, oscillations and flaws are avoided since the milling tool will not have an empty run or pass on the surface of the restoration 10.

In addition, the modified 3D constant milling strategy calculates a three-dimensional step width depending on the geometry of the processed surface that is constant in the direction of material removal. The consequence is that the tool/burr removes a constant amount of material from the restoration 10, independent of the surface geometry. Thus the cutting force between burr and ceramic restoration 10 is almost the same, and is independent of the steepness of the processed surface. Empty runs of burrs on the final surface of the restoration 10, and sudden changes in the amount of the removed material, both lead to uncontrolled oscillations/vibrations in the tool/burr that cause surface defects. Surface defects decrease the strength of the resultant ceramic dental restoration 10.

The milling of green state (non-sintered) zirconia is very different to the milling of metals and non-ceramics because of specific ceramic characteristics like brittleness, grain structure disturbing the normal milling process or abrasion and engagement of the tool. Milling zirconia is therefore a specific field and has special limitations.

Since the final quality of the machined surface has a direct influence on the fracture toughness, a smoother surface with a reduced number of flaws increases the strength. This effect, combined with the determination of areas or zones of increased stress in the restoration and only selectively machining these areas, results in a much better dental restoration by minimising the extra time effort of using this modified milling strategy only selectivity on the higher stress areas.

By combining a finite element analysis calculation with the calculation of the milling paths it is possible to determine higher stress areas of the restoration 10. For example, for a dental restoration 10 being formed as a five unit bridge framework, the finite element analysis to determine higher stress areas of the restoration 10 is performed in the same manner as for the calculation of the milling paths. A five unit bridge restoration 10 is designed with the outer units designed as hemispheric ball cups, and the counter bearing for the storage of the restoration 10 being ball end stumps. Force was applied at the outer pontics, not at the centre pontic. Due to the pivotable arrangement and a possible relative movement between the stumps an ideal four point bending test was simulated. The finite element analysis showed a maximum of stress at the bottom side of the connectors. The stress along the connectors with constant cross section was about the same. This is consistent with the theoretical results of a four point bending test. Therefore those areas of the restoration 10 with maximum stress could be located and localised.

It is possible to mark these areas and adapt the milling strategy automatically using design rules in the CAD/CAM software, or it is another option to mark these areas manually during the CAD design and adapt the milling paths of these marked areas as described. The manual marking of the CAD design could be undertaken by the dental technician, who often has experience and a sense of where the areas or zones of increased stress in the restoration 10 are likely to be located.

Figure 4:
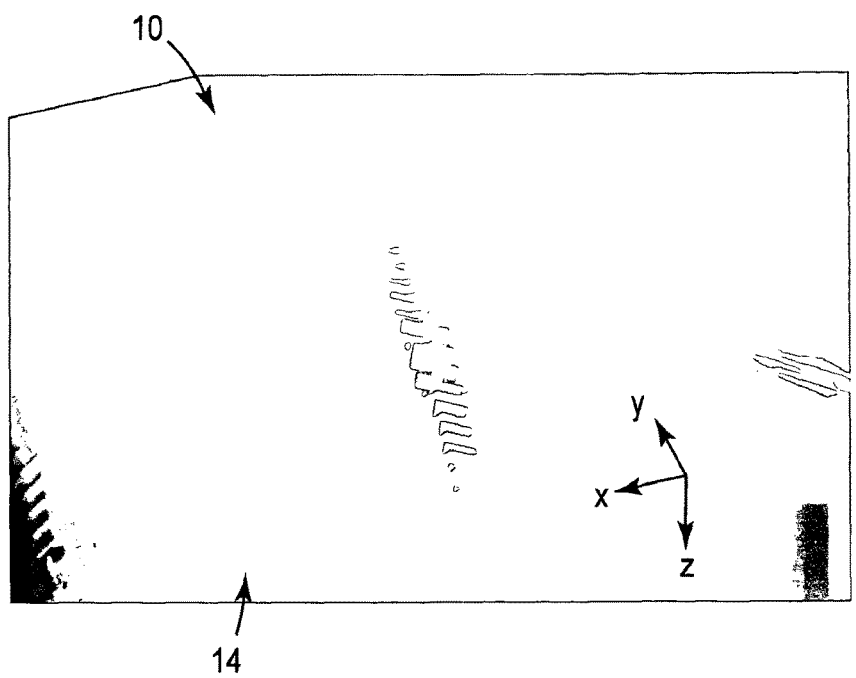
FIG. 4 shows a simulation of a milled ceramic dental restoration 10 having been manufactured using the modified milling path 16 of FIG. 3.

The below-mentioned milling parameters have shown best results in the milling machine of the 3M EPSE Lava™ digital dentistry system:
  Rotational speed: 11,500 rpm to 40,000 rpm
  Feeding: 400 mm/min to 2400 mm/min
  Axial step width: 0.05 mm to 0.8 mm
  Radial step width: 0.05 mm to 0.8 mm FIG. 4 shows a simulation of a milled ceramic dental restoration 10 having been manufactured using the modified milling path 16 of FIG. 3. It can be seen that the simulated milling tracks 14 are very uniform and the intersecting milling areas, as seen previously in FIG. 2, are avoided.

It has been found that by changing the milling strategy to modified 3D constant instead of the conventional combined milling strategy that separates the surface of the milled parts into flat and steep areas, it is possible to increase the mean value of initial fracture strength of the restoration by up to 25%, and also decrease the standard deviation.

Figure 5:
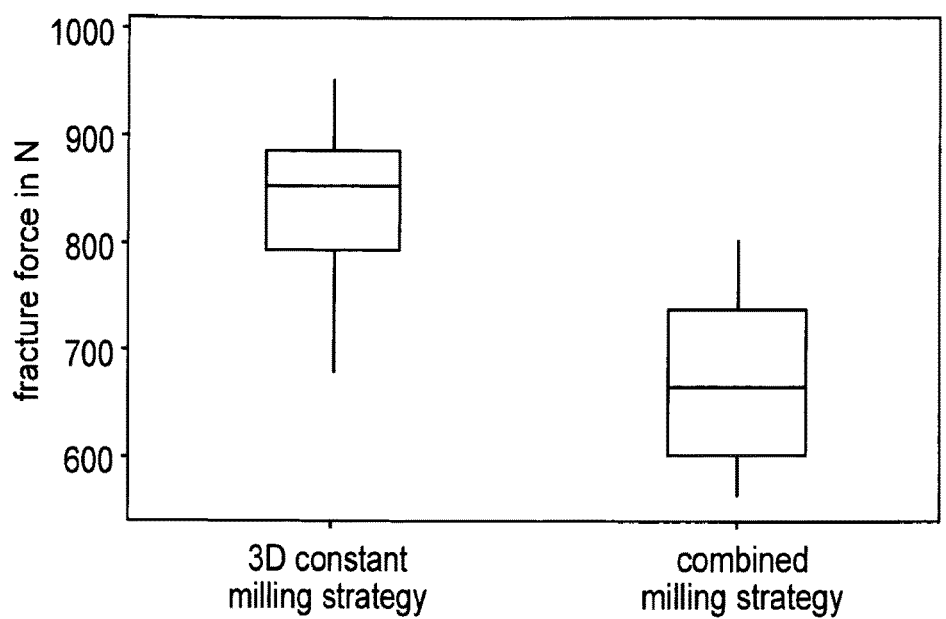
FIG. 5 is a graph of the comparative fracture strength of ten dental restorations formed from ceramic material #1 which have been produced using a modified milling strategy in accordance with the present invention, and compared to ten dental restorations which have been produced using known prior art milling strategies.
Figure 6:
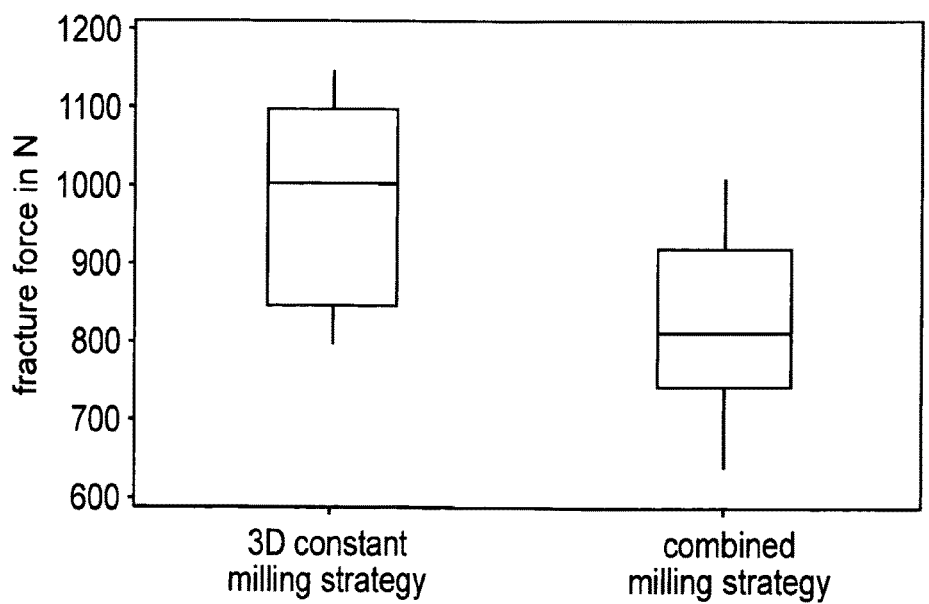
FIG. 6 illustrates a graph of the comparative fracture strength of ten dental restorations formed from ceramic material #2 which have been produced using a modified milling strategy in accordance with the present invention, and compared to ten dental restorations which have been produced using known prior art milling strategies.
Figure 7:
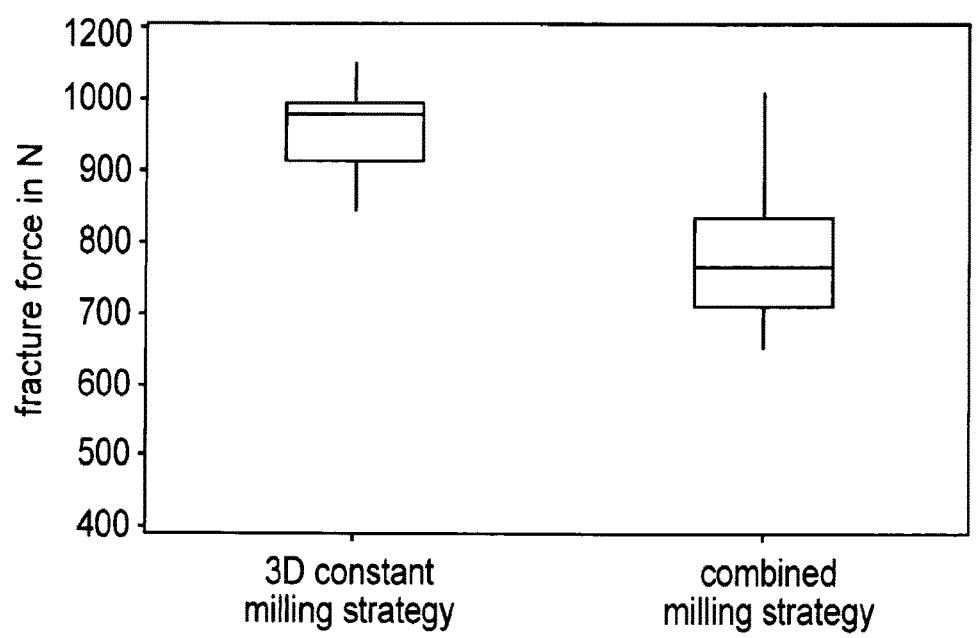
FIG. 7 shows a graph of the comparative fracture strength of ten dental restorations formed from ceramic material #3 which have been produced using a modified milling strategy in accordance with the present invention, and compared to ten dental restorations which have been produced using known prior art milling strategies.

FIGS. 5 to 7 show the comparative fracture strength of dental restorations formed from varying ceramic materials which have been produced using a modified milling path in accordance with the present invention and compared to known prior art combined milling strategies. The dental restoration was formed as a five unit bridge framework. In FIG. 5, two sets of ten dental restorations were prepared from a zirconia ceramic blank formed from 3M ESPE Lava™ Plus Zirconia Crown/Bridge Mill Blanks according to 3M ESPE™ Lava Frame manufacturer's instructions and denoted material #1. The CAD/CAM software in the 3M EPSE Lava™ system was used to machine the five unit bridge framework based on a three-dimensional dental restoration model. In the example shown in the left hand side of FIG. 5, a conventional combined milling strategy consisting of a rough and fine milling passes was used to mill the zirconia ceramic blank before the sintering stage.

In the left hand side of FIG. 5, a modified milling strategy according to the present invention was used. As described above, the CAD/CAM software was used to determine the areas or zones of increased stress in the three-dimensional dental restoration model to generate a modified milling path. Again rough and fine milling passes were used to mill the zirconia ceramic blank before the increased stress areas of the ceramic blank were selectively machined utilising the modified milling path. Finally the machined blank was then sintered according to 3M ESPE™ Lava Plus manufacturer's instructions at 1450° C.

Following sintering, the fracture strength of each of the ten dental restorations machined using a combined (standard 3M ESPE Lava™) milling strategy (the right hand of FIG. 5) and each of the ten dental restorations machined using a modified milling strategy according to the present invention (the left hand side of FIG. 5) were measured. For the purpose of the evaluation, each of the dental restorations was formed as a five unit bridge framework with three pontics. The outer units of the restoration having a hemispheric ball cup shape, with the pontics being solid and substantially shaped as a cuboid. The complete restoration was designed as monolithic framework without any kind of veneering. The restoration was designed with a large wall thickness of the outer units, so that fracture of the outer units was unlikely. The completed restoration is held in two cylindrical ball end stumps. The ball end stumps fit into the outer ball cup units with little play so that pivoting movement between the restoration and the stumps is possible. The advantage of this storage is that in case of bending the restoration, the deflection curve is not influenced by the support.

For the measurement of the fracture force a load is applied on each of the inner pontics, except the centre pontic. The arrangement of the applied force and the stumps as counter bearings is in accordance with a four point bending test of EN ISO NORM 6872. The advantage of this test is, that the applied forces cause constant stress between the force transmission points in sections with equal cross section, e.g. the area of the connectors. The applied force was slowly increased till the restoration fractured. The fracture of the restoration was detected and the maximum force was stored. The resultant fracture strengths are shown in FIG. 5 which clearly indicates a significant improvement in fracture strength using a modified milling strategy over conventionally-milled ceramic parts.

The measurement of fracture strength was repeated in two further sets of ceramic dental restorations, as shown in FIGS. 6 and 7. FIG. 6 shows the measured fracture strength of ceramic material #2 which was formed from 3M ESPE Lava™ Frame Zirconia Crown/Bridge Mill Blanks according to 3M ESPE™ Lava Frame manufacturer's instructions. Similarly, FIG. 7 shows the measured fracture strength of ceramic material #3 which was formed from 3M ESPE Lava™ Frame Zirconia Crown/Bridge Mill Blanks according to 3M ESPE™ Lava Frame manufacturer's instructions. For materials #2 and #3, the machined blank was sintered according to 3M ESPE™ Lava Frame manufacturer's instructions at a temperature of 1500° C. FIGS. 5 to 7 shows that an increase in fracture strength can be obtained in all samples #1 to #3 by using the modified milling strategy according to the present invention. The modified milling strategy also decreases the standard deviation in samples #2 and #3 which means that a more consistent and predictable restoration can be obtained.

A summary of the results from FIGS. 5 to 7 is shown in Table 1.

TABLE 1

| | Average fracture strength of restorations produced by modified 3D constant milling strategy (N) | Standard deviation of restorations produced by modified 3D constant milling strategy (N) | Average fracture strength of restorations produced by standard 3M ESPE Lava ™ milling strategy (N) | Standard deviation of restorations produced by standard 3M ESPE Lava ™ milling strategy (N) |
|---|---|---|---|---|
| Lava ™ Plus Sample #1 | 841 | 76 | 676 | 73 |
| Lava ™ Frame Sample #2 | 980 | 134 | 823 | 112 |
| Lava ™ Frame Sample #3 | 962 | 68 | 793 | 100 |

FIGS. 5 to 7 and Table 1 show that a significant increase in fracture strength is observed. The fracture strength of a ceramic part depends as much on the defects on the surface as the material strength. The lower the number of surface defects or flaws, the higher the fracture strength. The defects that are found in the green/white stage of the ceramic part are also present after firing in the final stage.

By increasing the fracture strength, the cross sectional area and wall thicknesses of dental parts can be significantly reduced. It is then possible to produce indications that were not available before, such as bridges for the lower jaw without disturbing visible connectors.

Although the method steps described herein are presented in a certain order the skilled person will recognise that certain steps can be arranged in a different order without departing from the invention.

What is claimed is:

1. A method of producing a dental restoration from a partially-sintered or non-sintered blank using a three-dimensional dental restoration model, the method comprising:
   generating, by a computer module, at least one or more first milling paths for rough and/or fine milling;
   determining, by the computer module, areas or zones of increased stress in the three-dimensional dental restoration model;
   generating, by the computer module and based on the determined areas or zones of increased stress, at least one modified milling path;
   machining the blank by milling utilising the one or more first milling paths;
   selectively machining parts of the blank utilising the at least one modified milling path to produce a machined blank; and
   sintering the machined blank.

2. The method according to claim 1, wherein the one or more first milling paths are determined by milling parameters selected from the group consisting of: blank starting materials and properties thereof, desired dental restoration surface quality and geometry, geometry and abrasion of the milling tool, economical parameters, computation time, parameters and specifications of the milling machine.

3. The method according to claim 1, wherein machining the blank by milling utilising one or more first milling paths further comprises:
   determining the one or more first milling paths;
   firstly machining the blank by infeeding a milling tool by a predetermined value in a vertical direction until a lowest milling point of the blank is reached; and
   secondly machining the blank by line-by-line milling.

4. The method according to claim 1, wherein determining areas or zones of increased stress in the three-dimensional dental restoration model is achieved using finite element analysis.

5. The method according to claim 1, wherein said dental restoration is formed from zirconium oxide or aluminium oxide ceramics.

6. The method according to claim 1, wherein the dental restoration is selected from the group consisting of: crowns, bridges, implants, dentures, tooth replacements, inlays, onlays and Maryland bridges.

7. The method according to claim 1, wherein the three-dimensional dental restoration model is obtained by scanning a dental impression or by performing an intraoral scan.

8. The method of claim 1, wherein determining, by the computer module, the areas or zones of increased stress comprises determining the areas or zones of increased stress in response to receiving data indicative of a user input manually identifying the areas or zones of increased stress in the three-dimensional dental restoration model.

9. The method of claim 1, wherein generating the at least one modified milling path comprises:
   generating the at least one modified milling path such that the at least one modified milling path does not intersect itself.

10. The method according to claim 1, wherein selectively machining parts of the blank utilising a modified milling path to produce a milled blank further comprises:
    determining a single second milling path that has a single point of entry between a milling tool and the blank and a single exit point, a cutting edge of the milling tool being in contact with the blank throughout.

11. The method according to claim 10, wherein determining a single second milling path that has a single point of entry between the milling tool and the blank and a single exit point ensures that no area of the blank is machined more than once.

12. The method according to claim 11, wherein determining a single second milling path that has a single point of entry between the milling tool and the blank and a single exit point further comprises:
    determining a constant three-dimensional step width milling path that is consistent in the direction of a burr removal.

13. The method according to claim 11, wherein the single second milling path does not intersect itself.

14. The method according to claim 11, wherein selectively machining parts of the blank utilising a single second milling path ensures that a constant amount of material is removed from the blank.

15. The method according to claim 11, wherein selectively machining parts of the blank utilising a single second milling path ensures that a cutting force between the tool and the blank is substantially the same and which depends on the geometry of the blank.

16. A computer-readable medium having computer-readable instructions which implement the following procedures:
   generating, by a computer module, a three-dimensional dental restoration model from scanned dental data;
   generating, by the computer module, at least one or more first milling paths for rough and/or fine milling a ceramic blank;
   determining, by the computer module, areas or zones of increased stress in the three-dimensional dental restoration model;
   generating, by the computer module and based on the determined areas or zones of increased stress, at least one modified milling path;
   machining the blank by milling utilising the one or more first milling paths;
   selectively machining parts of the blank utilising the at least one modified milling path to produce a machined blank; and
   sintering the machined blank.

17. A method of producing a dental restoration, the method comprising:
   producing a blank;
   machining the blank by milling utilising one or more first milling paths;
   selectively machining the blank in areas or zones of increased stress by milling utilising a second milling path that has a single point of entry between a cutting edge of a milling tool and the blank and a single exit point, the cutting edge of the milling tool being in contact with the blank throughout to produce a machined blank, wherein the second milling path does not intersect itself; and
   sintering the machined blank.

* * * * *